US012661631B2

(12) United States Patent
Mehr et al.

(10) Patent No.: US 12,661,631 B2
(45) Date of Patent: *Jun. 23, 2026

(54) LEAK DETECTION AND/OR PREVENTION FOR HIGH TEMPERATURE THERMAL PROCESS SYSTEMS

(71) Applicant: Honeywell International Inc., Charlotte, NC (US)

(72) Inventors: Mehrad Mehr, Morristown, NJ (US); Bahram Jadidian, Watchung, NJ (US)

(73) Assignee: Honeywell International Inc., Charlotte, NC (US)

( * ) Notice: Subject to any disclaimer, the term of this patent is extended or adjusted under 35 U.S.C. 154(b) by 710 days.

This patent is subject to a terminal disclaimer.

(21) Appl. No.: 17/937,352

(22) Filed: Sep. 30, 2022

(65) Prior Publication Data

US 2024/0109049 A1 Apr. 4, 2024

(51) Int. Cl.
*B01J 19/24* (2006.01)
*B01J 6/00* (2006.01)
(Continued)

(52) U.S. Cl.
CPC ............... *B01J 19/24* (2013.01); *B01J 6/008* (2013.01); *B01J 19/0013* (2013.01); *C01B 3/24* (2013.01);
(Continued)

(58) Field of Classification Search
CPC ........ B01J 19/24; B01J 6/008; B01J 19/0013; B01J 2219/00155; B01J 2219/00164;
(Continued)

(56) References Cited

U.S. PATENT DOCUMENTS 3,166,305 A * 1/1965 Troglione .............. C21D 1/773
432/237
3,721,429 A 3/1973 Young et al.
(Continued)

FOREIGN PATENT DOCUMENTS

CN 201447458 U 5/2010
CN 205423823 U 8/2016
(Continued)

OTHER PUBLICATIONS

Childers et al., "Chemical Vapor Deposition Methane Pyrolysis Enables Closed-Loop Oxygen Recovery: Reducing System Consumables," ICES 2021-33 50th International Conference on Environmental Systems, Jul. 12-15, 2021, 10 pp.
(Continued)

*Primary Examiner* — Stuart L Hendrickson
(74) *Attorney, Agent, or Firm* — Shumaker & Sieffert, P.A.

(57) ABSTRACT

A thermal process system includes a retort assembly that includes a retort chamber, a heating assembly configured to heat the retort chamber, a vessel housing, a process gas inlet, and a sealing gas inlet. The retort assembly is configured to substantially contain one or more process gases in the retort chamber during a thermal process. The vessel housing is positioned around the retort chamber and configured to maintain a pressure or vacuum within the retort chamber. The process gas inlet is configured to receive the one or more process gases into the retort assembly. The sealing gas inlet is configured to receive a sealing gas into the vessel housing. The thermal process system may further include a leak gas detector configured to detect a presence of a leak gas, in which the leak gas includes a gas that is not the one or more process gases in the retort chamber.

20 Claims, 4 Drawing Sheets

(51) Int. Cl.

| | |
|---|---|
| *B01J 19/00* | (2006.01) |
| *C01B 3/24* | (2006.01) |
| *C01B 32/05* | (2017.01) |
| *C07C 1/12* | (2006.01) |
| *G01M 3/04* | (2006.01) |

(52) U.S. Cl.

CPC ................ *C01B 32/05* (2017.08); *C07C 1/12* (2013.01); *B01J 2219/00155* (2013.01); *B01J 2219/00164* (2013.01); *C01B 2203/0272* (2013.01); *C01B 2203/1241* (2013.01); *G01M 3/04* (2013.01)

(58) Field of Classification Search

CPC ... C01B 32/05; C01B 3/24; C01B 2203/0272; C01B 2203/1241; C07C 1/12; G01M 3/04

See application file for complete search history.

(56) References Cited

U.S. PATENT DOCUMENTS

| | | | | |
|---|---|---|---|---|
| 4,056,602 | A | * | 11/1977 | Matovich ............... C10G 15/08 |
| | | | | 423/349 |
| 4,551,206 | A | | 11/1985 | Deering et al. |
| 5,032,079 | A | | 7/1991 | Tsuchiya et al. |
| 9,115,414 | B2 | | 8/2015 | Korecki et al. |
| 10,093,864 | B2 | | 10/2018 | Tandon |
| 10,479,739 | B2 | | 11/2019 | Yates et al. |
| 10,486,967 | B2 | | 11/2019 | Isobe et al. |
| 10,519,047 | B2 | | 12/2019 | Johnson et al. |
| 10,889,771 | B2 | | 1/2021 | O'grady |
| 2011/0114621 | A1 | | 5/2011 | Sarres et al. |

FOREIGN PATENT DOCUMENTS

| | | | |
|---|---|---|---|
| CN | 110284216 | A | 9/2019 |
| DE | 3733078 | A1 | 4/1989 |
| EP | 2330325 | A2 | 6/2011 |
| JP | H05248765 | A | 9/1993 |
| JP | 2007333277 | A | 12/2007 |
| WO | 2010009701 | A2 | 1/2010 |

OTHER PUBLICATIONS

Childers et al., "Chemical Vapor Deposition Methane Pyrolysis Enables Closed-Loop Oxygen Recovery: Path to Flight," ICES 2022-390 51st International Conference on Environmental Systems, St. Paul, MN, Jul. 10-14, 2022, 13 pp.

Yates et al., "Hydrogen Recovery by Methane Pyrolysis to Elemental Carbon," ICES 2019-103, 49th International Conference on Environmental Systems, Boston, MA, Jul. 7-11, 2019, 16 pp.

\* cited by examiner

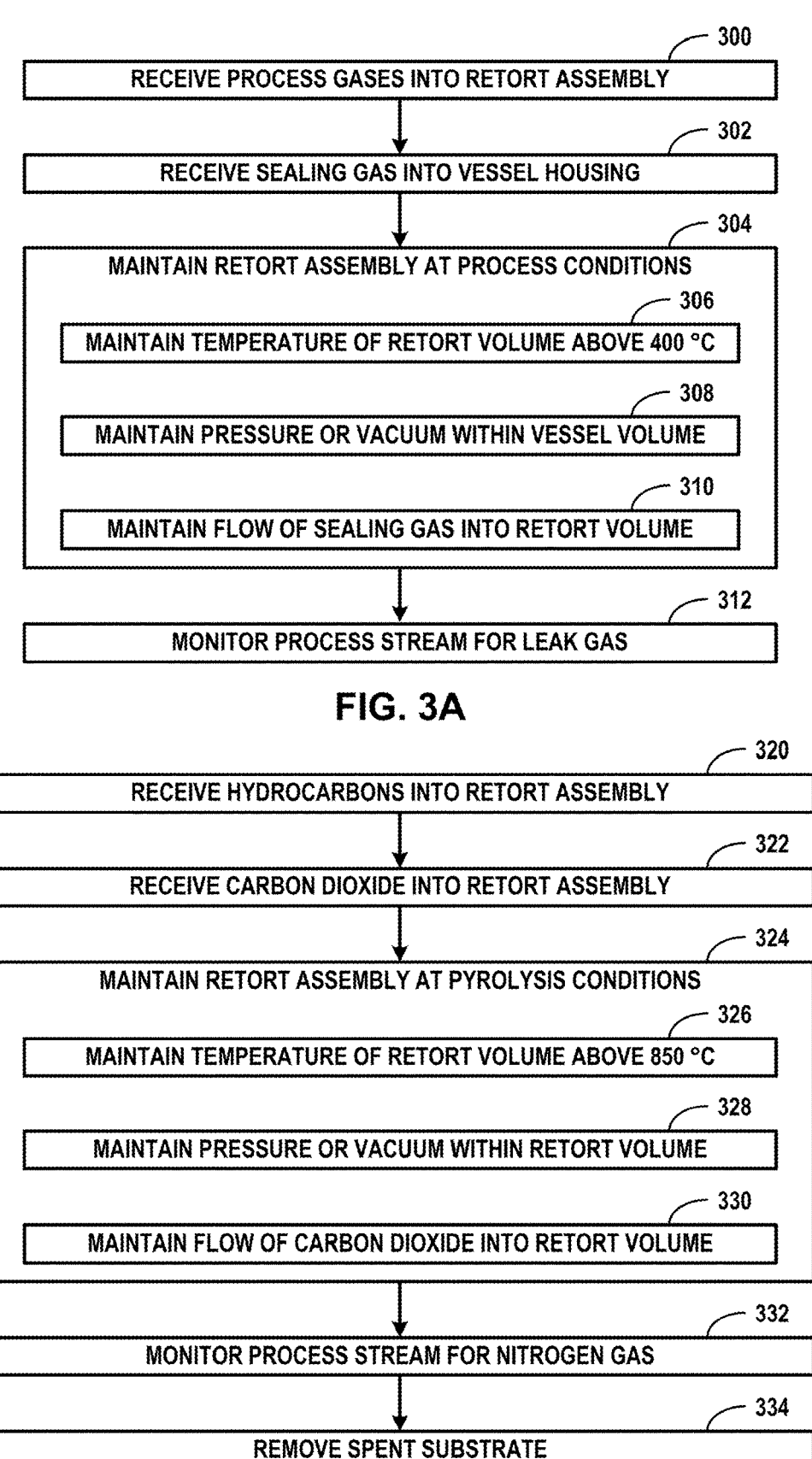

RECEIVE PROCESS GASES INTO RETORT ASSEMBLY ⌐ 300

RECEIVE SEALING GAS INTO VESSEL HOUSING ⌐ 302

MAINTAIN RETORT ASSEMBLY AT PROCESS CONDITIONS ⌐ 304

MAINTAIN TEMPERATURE OF RETORT VOLUME ABOVE 400 °C ⌐ 306

MAINTAIN PRESSURE OR VACUUM WITHIN VESSEL VOLUME ⌐ 308

MAINTAIN FLOW OF SEALING GAS INTO RETORT VOLUME ⌐ 310

MONITOR PROCESS STREAM FOR LEAK GAS ⌐ 312

FIG. 3A

RECEIVE HYDROCARBONS INTO RETORT ASSEMBLY ⌐ 320

RECEIVE CARBON DIOXIDE INTO RETORT ASSEMBLY ⌐ 322

MAINTAIN RETORT ASSEMBLY AT PYROLYSIS CONDITIONS ⌐ 324

MAINTAIN TEMPERATURE OF RETORT VOLUME ABOVE 850 °C ⌐ 326

MAINTAIN PRESSURE OR VACUUM WITHIN RETORT VOLUME ⌐ 328

MAINTAIN FLOW OF CARBON DIOXIDE INTO RETORT VOLUME ⌐ 330

MONITOR PROCESS STREAM FOR NITROGEN GAS ⌐ 332

REMOVE SPENT SUBSTRATE ⌐ 334

FIG. 3B

LEAK DETECTION AND/OR PREVENTION FOR HIGH TEMPERATURE THERMAL PROCESS SYSTEMS

GOVERNMENT RIGHTS

This invention was made with Government support under Grant Contract Number 80MSFC21CA010 awarded by NASA. The Government has certain rights in the invention.

TECHNICAL FIELD

The present disclosure relates to systems and techniques for maintaining thermal process conditions.

BACKGROUND

An environmental control system (ECS) of a structure, such as a building or vehicle, may remove carbon dioxide expelled by occupants of an environment, such as a room or cabin, to maintain comfort and safety. In some instances, the carbon dioxide may be absorbed from the environment by a liquid sorbent and desorbed from the liquid sorbent for discharge from the structure. However, for an atmosphere limited structure, such as a spacecraft or submarine, such discharge of carbon dioxide may waste oxygen from the carbon dioxide that may otherwise be recovered. To extract oxygen from the carbon dioxide, the ECS may react the carbon dioxide with hydrogen gas to form methane through a Sabatier reaction. The ECS may produce at least a portion of this hydrogen gas by pyrolyzing methane. Methane pyrolysis occurs at a relatively high temperature, and may require heavy equipment to seal the gases.

SUMMARY

In general, the disclosure describes thermal process systems, such as reactor systems, configured to prevent leaks of reactive gases out of, and/or detect leaks of reactive or nonreactive gases into, a reactor volume. For example, a retort assembly includes a retort chamber and a retort lid that form a non-hermetic seal to substantially contain reactant gases in the retort chamber during a thermal process. A vessel housing positioned around the retort chamber forms a hermetic seal around the retort assembly to maintain a pressure within the retort chamber. A sealing gas inlet receives a sealing gas into the vessel housing to provide a small amount of positive flow across the non-hermetic seal of the retort chamber and retort lid. The sealing gas does not substantially interfere with the thermal process, and may include an inert gas already present in the gas stream received by the retort assembly or a gas that is consumed in a downstream process. A leak gas detector may be positioned downstream of the retort assembly to detect a presence of a leak gas. The leak gas may be a gas that is not ordinarily present in the retort chamber, such as gases that are not reactants, products, or byproducts of the thermal process. In this way, outflow of reactants may be reduced or prevented and/or inflow of ambient gases may be quickly detected and addressed.

In some examples, the disclosure describes a thermal process system that includes a retort assembly, a heating assembly, a vessel housing, a process gas inlet, and a sealing gas inlet. The retort assembly includes a retort chamber and is configured to substantially contain one or more process gases in the retort chamber during a thermal process. The heating assembly includes one or more heating elements and is configured to heat the retort chamber. The vessel housing is positioned around the retort chamber and the one or more heating elements and is configured to maintain a pressure within the retort chamber. The process gas inlet is configured to receive the one or more process gases into the retort assembly. The sealing gas inlet is configured to receive a sealing gas into the vessel housing. In some examples, the thermal process system may further include a gas outlet configured to discharge one or more process gases from the retort chamber and a leak gas detector downstream of the gas outlet and configured to detect a presence of a leak gas, in which the leak gas includes a gas that is not the one or more process gases in the retort chamber.

In some examples, the disclosure describes a system for recovering carbon. The system includes a pyrolysis reactor configured to generate hydrogen gas from a hydrocarbon through pyrolysis. The pyrolysis reactor includes a retort assembly, a heating assembly, a vessel housing, a process gas inlet, and a carbon dioxide inlet. The retort assembly includes a retort chamber and is configured to substantially contain the hydrocarbon and the hydrogen gas in the retort chamber during the pyrolysis and house one or more fibrous substrates defining a deposition surface for the carbon generated from the pyrolysis. The heating assembly includes one or more heating elements and is configured to heat the retort chamber. The vessel housing is positioned around the retort chamber and the one or more heating elements and is configured to maintain a pressure or vacuum within the retort chamber. The process gas inlet is configured to receive the hydrocarbon into the retort chamber. The carbon dioxide inlet is configured to receive carbon dioxide from a carbon dioxide source into the vessel housing. In some examples, the system may further include a leak gas detector configured to detect a presence of a leak gas, in which the leak gas includes a gas that is not the one or more process gases in the retort chamber.

In some examples, the disclosure describes a method that includes receiving, by a retort chamber of a retort assembly of a thermal process system, one or more process gases and receiving, by a vessel housing positioned around the retort chamber, a sealing gas. The method further includes maintaining, by the thermal process system, the one or more process gases at thermal process conditions in the retort chamber. Such maintenance is achieved by at least maintaining a temperature of the one or more process gases in a retort volume within the retort chamber above about 400° C., maintaining a pressure boundary between a vessel volume within the vessel housing and an environment external to the vessel housing, and maintaining a flow of the sealing gas from the vessel volume into the retort volume to substantially prevent outflow of the one or more process gases at the thermal process conditions.

The details of one or more examples are set forth in the accompanying drawings and the description below. Other features, objects, and advantages will be apparent from the description and drawings, and from the claims.

BRIEF DESCRIPTION OF THE FIGURES

The details of one or more examples are set forth in the accompanying drawings and the description below. Other features, objects, and advantages will be apparent from the description and drawings, and from the claims.

FIG. 3A is a flowchart of an example technique for reacting gases.

FIG. 3B is a flowchart of an example technique for pyrolyzing hydrocarbons.

DETAILED DESCRIPTION

Figure 1A:
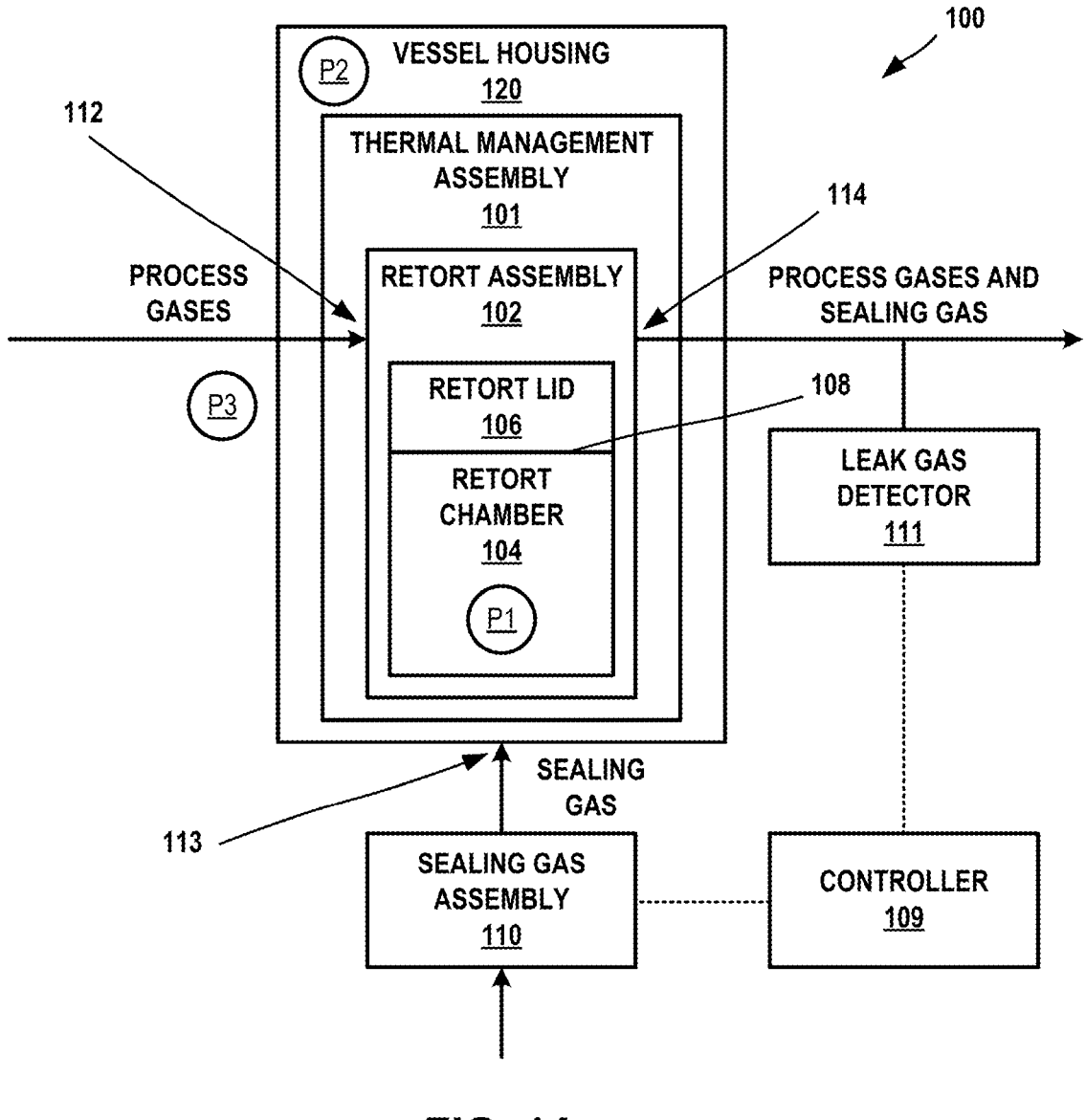
FIG. 1A is a schematic block diagram illustrating an example thermal process system.

In general, the disclosure describes thermal process systems for reducing leaks at pressurized or vacuum conditions and/or detecting leaks at vacuum conditions. Thermal process systems may separately contain process gases within an inner gaseous boundary provided by an inner retort assembly and maintain a pressure or vacuum within an outer pressure boundary provided by an outer vessel housing. At steady state conditions, containment of the inner retort assembly within the pressure boundary may result in a low or negligible pressure differential across the inner retort assembly. However, during non-equilibrium conditions, temporary transient temperature fluctuations within the inner retort assembly may result in a non-zero pressure differential across the inner retort assembly, resulting in outflow of process gases from the inner retort assembly. For example, heating elements may go off briefly to address a temperature overshoot followed by subsequent cooling. As the thermal process system cools, the temperature of gases in the outer vessel housing may drop faster than gases within the inner retort assembly due to proximity to a cooling source, resulting in lower pressure in the vessel housing relative to the pressure in the inner retort assembly. Additionally or alternatively, the outer vessel housing or other components of the system maintaining the outer pressure boundary, such as an upstream or downstream piping or equipment, may develop leaks, such as by failed O-rings, particles on O-rings, or corrosion in metallic or plastic pining systems, thereby introducing ambient air or other gases into the inner retort assembly.

According to the principles of the disclosure, thermal process systems described herein may reduce or prevent outflow of gases from the inner retort assembly by providing flow of a sealing gas across a non-hermetic seal formed by the inner retort assembly. The flow of the sealing gas may be sufficiently high to provide flow of the sealing gas across the non-hermetic seal during temporary transient temperature fluctuations. The sealing gas may be a gas that does not interfere with thermal processes of the process gases in the inner retort assembly, but may undergo one or more thermal processes downstream of the inner retort assembly. For example, in a carbon recovery process, carbon dioxide may be used to seal a methane pyrolysis reactor producing hydrogen gas, and later used as a reactant with hydrogen gas in a Sabatier reactor under different operating conditions to produce methane and water. In this way, thermal process systems may reduce outflow of process gases without substantially affecting thermal process conditions or introducing an unnecessary volume of gases into the thermal process system.

Additionally or alternatively, thermal process systems described herein may detect inflow of gases into inner retort assembly by detecting a presence of a leak gas downstream of the inner retort assembly. The leak gas may include an inert gas from an ambient atmosphere that is not present in the thermal process system or any other systems upstream of the thermal process system. For example, in a carbon recovery process, a presence or concentration of nitrogen gas from the ambient atmosphere may be detected to indicate a presence or rate of progression of a leak in either the thermal process system or another point in the system. In this way, thermal process systems may continuously detect inflow of ambient air into the thermal process system.

Thermal process systems may be configured to operate with reduced outflow of process gases by maintaining flow of a sealing gas across a non-hermetic seal of a retort assembly. FIG. 1A is a schematic block diagram illustrating an example thermal process system 100. Thermal process system 100 may be configured to maintain thermal process conditions and contain various process gases at a process pressure or vacuum P1. Thermal process system 100 may be used for a variety of high temperature (e.g., >400° C., or higher than a thermal degradation temperature of gasket sealing materials) thermal processes that may involve a pressure differential including, but not limited to, reactions, such as methane pyrolysis, heating, inerting, and the like.

Thermal process system 100 includes a retort assembly 102 configured to provide a retort volume for processing one or more process gases. Retort assembly 102 is configured to substantially contain one or more process gases during a thermal process. To reduce thermal losses from thermal process system 100, a seal defining a containment boundary of the process gases may be preferably in a high temperature region of thermal process system 100, such as part of retort assembly 102.

Thermal process system 100 includes a thermal management assembly 101 configured to maintain a high temperature environment within retort assembly 102. As will be described below, thermal management assembly 101 may include a heating assembly configured to heat process gases within retort assembly 102 and insulative and/or reflective materials configured to reduce heat transfer from retort assembly 102. As a result, thermal management assembly 101 may consume relatively low amounts of power to maintain the thermal process conditions within retort assembly 102.

To enable high temperature operation of retort assembly 102, hermetic sealing of gases within thermal process system 100, and substantial containment of gases within retort assembly 102, thermal process system 100 is configured to separate the hermetic, pressure boundary characteristic for maintaining a pressure within thermal process system 100 from the gas containment boundary characteristic for containing the gases within retort assembly 102. By providing these gas containment and pressure containment functions using separate structures and positioning the gas containment within the pressure containment, retort assembly 102 may be capable of containing gases at high temperatures (e.g., greater than 400° C.) and limiting gaseous exchanges inside reaction system 200 without forming a hermetic seal.

To maintain process pressure P1 within retort assembly 102, thermal process system 100 includes a vessel housing 120 configured to provide a pressurized (e.g., pressure above or below ambient pressure), hermetically-sealed environment for processing one or more gases. Vessel housing 120 is configured to form a pressure boundary for gases in thermal process system 100. Vessel housing 120 may be at a relatively low temperature due to heat containment provided by thermal management assembly 101, such that a variety of reusable sealing mechanisms may be used to provide a hermetic seal between an external pressure P3 and the reaction pressure P1, such as O-rings.

Vessel housing 120 is positioned around retort assembly 102 and thermal management assembly 101. As a result, retort assembly 102 is subject to a reduced pressure difference between a retort volume within retort assembly 102 and a vessel volume outside retort assembly 102. Due to the reduced pressure difference across retort assembly 102, the containment boundary may be at least partially maintained using sealing mechanisms configured to seal gases driven by a concentration gradient. These sealing mechanisms may be more resistant to heat than polymer-based sealing mechanisms, enabling retort assembly 102, and correspondingly the sealing mechanism, to be positioned within and operated at a high temperature.

In the example of FIG. 1A, retort assembly 102 includes a retort chamber 104, a removable retort lid 106, a process gas inlet 112, and a gas outlet 114. Process gas inlet 112 is configured to receive one or more process gases into retort chamber 104 and gas outlet 114 is configured to discharge one or more process gases from retort chamber 104. Retort assembly 102 is configured to substantially contain one or more process gases in retort chamber 104 during a thermal process. For example, retort chamber 104 and retort lid 106 may define a reaction volume in which one or more reaction gases undergo a reaction, such that retort chamber 104 and retort lid 106 may contain reaction and product gases for a residence time. Retort lid 106 may be configured to contact a wall of retort chamber 104 at a sealing interface 108. Sealing interface 108 between retort lid 106 and retort chamber 104 may be configured to form a contact seal between retort lid 106 and retort chamber 104. This contact seal may be non-hermetic and may not include a gasket or other potentially degradable material.

Thermal process system 100 may be configured to maintain a pressure or vacuum within vessel housing 120, including within retort assembly 102 positioned within vessel housing 120, to reduce a pressure differential across retort assembly 102. At steady state conditions, process gases in retort assembly 102 within the pressure boundary maintained by vessel housing 120 may be subject to relatively small variations in pressure and temperature. However, during non-equilibrium conditions, temporary transient temperature fluctuations within the outer vessel housing 120 and inner retort assembly 102 may result in variation in pressure differential across sealing interface 108 of retort assembly 102, and correspondingly may result in outflow of process gases from retort assembly 102 across sealing interface 108. Such outflow of process gases may result in damage to components within vessel housing 120, such as by depositing carbon that may cause electrical shorts, changing thermal conductivity of insulation, reacting with structural components, or corroding structural components.

To reduce or prevent outflow of gases from retort assembly 102, thermal process system 100 is configured to provide a flow of a sealing gas across sealing interface 108 of retort assembly 102. Retort assembly 102 includes a sealing gas inlet 113 configured to receive a sealing gas into vessel housing 120. Thermal process system 100 may include a sealing gas assembly 110 fluidically coupled to sealing gas inlet 113 and configured to control flow of the sealing gas into vessel housing 120. For example, sealing gas assembly 110 may include a flow meter configured to measure the flow of the sealing gas into vessel housing 120 and a control valve configured to control a flow of the sealing gas into vessel housing 120 to substantially prevent outflow of the one or more process gases from the retort assembly.

Flow of the sealing gas may be sufficiently high to provide flow of the sealing gas across the non-hermetic sealing interface 108 during slight temperature fluctuations experienced during operation of thermal process system 100. The sealing gas may be a gas that does not substantially interfere with thermal processes of the process gases in retort assembly 102. For example, the sealing gas may be an inert gas that does not react with process gases in retort assembly 102 at operating temperatures within retort assembly 102, does not substantially (e.g., within a general service timeframe) damage structural or electrical components at operating conditions within retort assembly 102, does not substantially accumulate in thermal process system 100 or systems fluidically coupled to thermal process system 100, does not substantially lower thermal process efficiency of thermal process system 100, and/or does not deposit or condense in thermal process system 100. Flow of the sealing gas may be sufficiently low so as to not substantially increase a heating load of the retort assembly. For example, the flow of the sealing gas may be sufficient to substantially prevent outflow in response to pressure differentials of less than about 10 psig. In this way, thermal process system 100 may reduce outflow of process gases without substantially affecting thermal process conditions.

In some examples, the sealing gas may include a precursor to or derivative of one or more process gases in retort assembly 102. A precursor to or derivative of one or more process gases may include any gas that is consumed or produced in another process fluidically coupled to thermal process system 100. As one example, the sealing gas may be relatively inert during a thermal process within retort assembly 102, but may undergo one or more thermal processes upstream or downstream of retort assembly 102, such that the sealing gas is at least partially consumed. As another example, the sealing gas may be reactive during a thermal process within retort assembly 102, but may be relatively small or negligible compared to other process gases. In this way, thermal process system 100 may reduce outflow of process gases without introducing an unnecessary volume of gases into thermal process system 100 or other systems fluidically coupled to thermal process system 100.

In some examples, the sealing gas includes carbon dioxide. For example, in a carbon recovery process such as described in FIG. 2B below, carbon dioxide may be used to seal a methane pyrolysis reactor producing hydrogen gas, and later used as a reactant with hydrogen gas in a Sabatier reactor under different operating conditions to produce methane and water.

Various process fluctuations within thermal process system 100 may also affect containment of gases within the pressure boundary of vessel housing 120 or another pressure boundary upstream or downstream of thermal process system 100. As one example, temperature fluctuations of vessel housing 120 or other components of thermal process system 100 maintaining the pressure boundary may cause leaks to develop in thermal process system 100, thereby introducing ambient air or other gases into retort assembly 102 along with sealing gas via vessel housing 120. As another example, temperature fluctuations of other systems fluidically coupled to thermal process system 100 may cause leaks to develop in the other systems, thereby introducing ambient air or other gases into retort assembly 102 along with process gases via process gas inlet 112. As a result of the leak, process gases discharged from retort assembly 102 may include one or more leak gases that are not process gases in thermal process system 100 and/or systems fluidically coupled to thermal process system 100.

To detect a presence of a leak gas in retort assembly 102, thermal process system 100 includes a leak gas detector 111 downstream of gas outlet 114. Leak gas detector 111 is configured to detect a presence of one or more leak gases in the gases discharged from retort assembly 102. The presence and/or characteristics of the leak gas may indicate a leak in thermal process system 100 or a system fluidically coupled to thermal process system 100. For example, to indicate presence or worsening of a leak, leak gas detector 111 may detect a concentration of the leak gas that is above a threshold or is higher than a previous concentration measurement.

The leak gas may include a gas that is not one of the process gases in retort assembly 102 for either the thermal process within thermal process system 100 or a process for a system upstream of thermal process system 100. For example, the gases in retort assembly 102 may include process gases for the present thermal process, the sealing gas for flowing across sealing interface 108, and/or gases involved in or produced by processes upstream of thermal process system 100. The gases involved in or produced by processes upstream of thermal process system 100 may remain in a process flow of thermal process system 100 and other systems for a period of time, such that their presence may not indicate a leak.

The leak gas may include a gas or a derivative of a gas that is present in an ambient environment of thermal process system 100 or a system fluidically coupled to thermal process system 100. In some examples, the leak gas includes nitrogen. For example, in a carbon recovery process such as described in FIG. 2B below, carbon dioxide may be used to seal a methane pyrolysis reactor producing hydrogen gas, and later used as a reactant with hydrogen gas in a Sabatier reactor under different operating conditions to produce methane and water.

While illustrated as a single leak gas detector 111 positioned downstream of gas outlet 114, thermal process system 100 may include leak gas detectors located at other positions. For example, to detect whether a leak is coming from thermal process system 100, another leak gas detector may be positioned at process gas inlet 112 to detect a presence or concentration of a leak gas entering retort assembly 102.

Thermal process system 100 includes a controller 109 configured to control one or more thermal processes in thermal process system 100. Controller 109 may be communicatively coupled to components of thermal process system 100, such as measurement and/or control equipment of thermal management assembly 101, retort assembly 102, process gas inlet 112, gas outlet 114, sealing gas assembly 110, leak gas detector 111, or any other components involved in control of thermal process conditions within retort assembly 102.

Controller 109 may include any of a wide range of devices, including control circuitry, processors (e.g., one or more microprocessors, one or more application specific integrated circuits (ASICs), one or more field programmable gate arrays (FPGAs), or the like), processing circuitry, one or more servers, one or more desktop computers, one or more notebook (i.e., laptop) computers, one or more cloud computing clusters, or the like, configured to implement functionality and/or process instructions for execution within controller 109. For example, processing circuitry may be capable of processing instructions stored in a memory. A memory may be configured to store information within controller 109 during operation. The memory may include a computer-readable storage medium or computer-readable storage device. In some examples, the memory includes one or more of a short-term memory or a long-term memory. The memory may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, the memory is used to store program instructions for execution by processing circuitry 102.

Controller 109 may be configured to control thermal process system 100 to maintaining the process gases at thermal process conditions in retort chamber 104. For example, controller 109 may be configured to control thermal management assembly 101 to maintain a temperature of the process gases in a retort volume within retort chamber 104 above about 400° C., control one or more pressure assemblies, such as a control valve or pressurizing equipment, to maintain a pressure of the process gases, and control of other components associated with the thermal process of thermal process system 100.

Controller 109 may be configured to control sealing gas assembly 110 to maintain a flow of the sealing gas from the vessel volume into the retort volume to substantially prevent outflow of the one or more process gases at the thermal process conditions. For example, controller 109 may be configured to control a control valve or other flow control device to provide a flow of the sealing gas. In some instances, controller 109 may be configured to control the flow of the sealing gas such that the sealing gas continuously flows into retort assembly 102 during the thermal process. For example, controller 109 may provide a flow of sealing gas that is greater than a flow threshold, such as indicated by a flow rate measurement or pressure measurement. In some instances, controller 109 only flow the sealing gas during transients or other operations with a higher likelihood of outflow of process gases from retort assembly 102. For example, sealing interface 108 may be configured to prevent outflow of process gases at relatively low pressure differentials experienced at steady state, but may not be capable of preventing outflow of process gases due to variations in pressure experienced during transient conditions. As such, controller 109 may flow sealing gas during such transient conditions.

In some examples, controller 109 may be configured with one or more interlocks that modify flow of the sealing gas based on conditions within thermal process system 100. For example, an increase in pressure within vessel housing 120 may indicate that sealing interface 108 has sealed, such as due to carbon build-up. In response to an indication of a higher pressure, controller 109 may be configured to stop flow of the sealing gas into vessel housing 120. Further operation of controller 109 may be described in the methods of FIGS. 3A and 3B below.

Figure 1B:
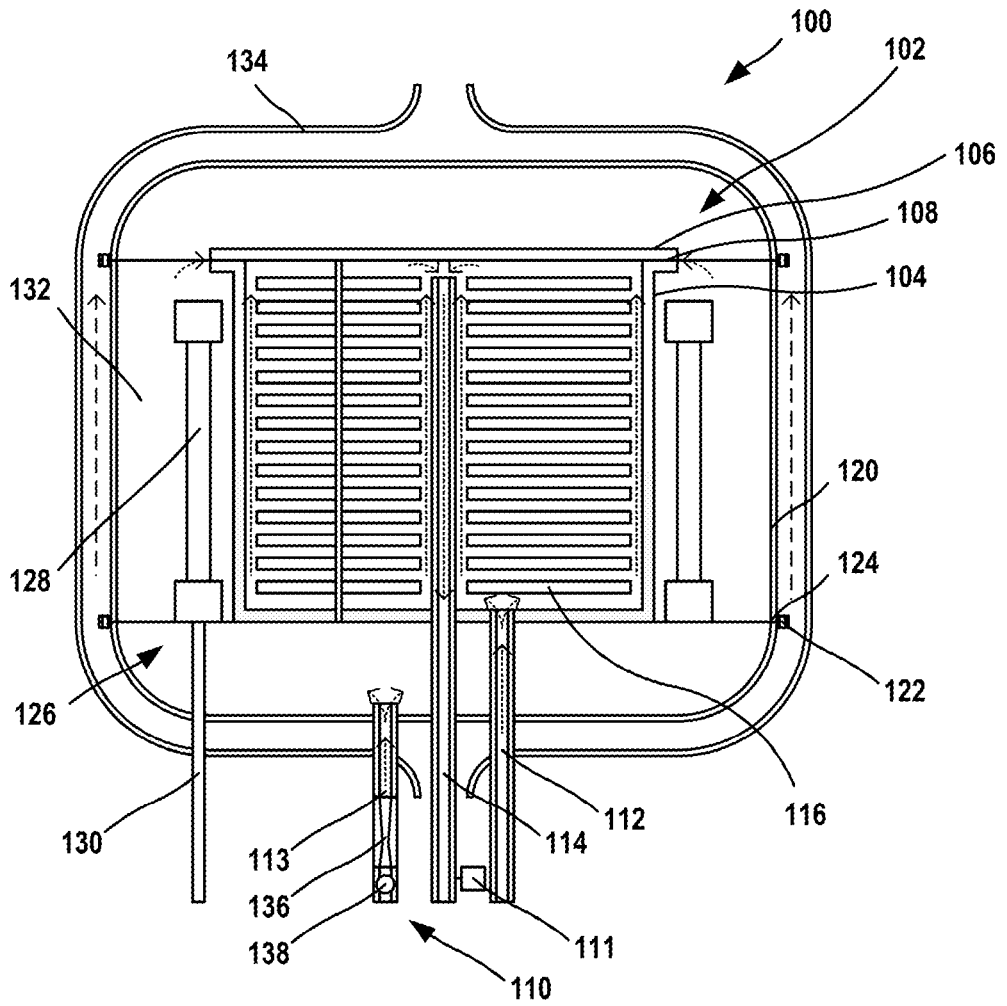
FIG. 1B is a cross-sectional side view diagram illustrating an example thermal process system for generating hydrogen gas from hydrocarbons.

Thermal process systems configured to operate with reduced outflow of process gases may include thermal process systems for generating hydrogen gas from hydrocarbons. For example, outflow of hydrocarbons from a methane pyrolysis reactor may result in pyrolysis of the hydrocarbons outside the controlled retort volume, resulting in reduced hydrogen gas generation and increased clean-up. FIG. 1B is a cross-sectional side view diagram illustrating an example thermal process system 100 for generating hydrogen gas from hydrocarbons, such as may be used for pyrolysis reactors described in FIG. 2A below. However, in other examples, thermal process system 100 may be used for reactions other than methane pyrolysis that proceed at high temperatures and pressure or vacuum environments.

Thermal process system 100 includes a retort assembly 102. In the example of FIG. 1A, retort assembly 102 includes a retort chamber 104 and a removable retort lid 106. Retort assembly 102 is configured to substantially contain one or more gases in retort chamber 104 during a reaction. For example, retort chamber 104 and retort lid 106 may define a reaction volume in which one or more gases undergo a reaction. Retort chamber 104 and retort lid 106 may have a variety of shapes. In the example of FIG. 1B, retort assembly 102 may be configured for general flow along an axis of retort chamber 104, such that gases, such as hydrocarbon gases, may be continuously received and product gases, such as hydrogen gas, reaction byproducts, and unreacted hydrocarbon gases, may be continuously discharged from thermal process system 100. Retort chamber 104 may be sized to have a particular residence time and pressure drop for a particular flow rate of gases and particular void fraction of one or more fibrous substrates 116.

During a thermal process, such as a reaction, heating, or inerting process, the retort volume within retort chamber 104 may be at relatively high temperatures. For example, the reaction volume may have a temperature greater than about 850° C. As such, retort chamber 104 and retort lid 106 may be configured for exposure to relatively high temperatures. In some examples, each of retort lid 106 and retort chamber 104 includes non-metallic materials, such as graphite, a ceramic, or a ceramic matrix composite. Non-metallic materials may be stronger and more resistant to creep, corrosion, instabilities, or other high temperature structural defects than metals. In some examples, a surface of retort chamber 104 and retort lid 106 may include a ceramic coating or other coating compatible with particular gases contained within retort chamber 104. As such, provided acceptable high-temperature strength and toughness, the properties of interest for materials of retort chamber 104 and retort lid 106 may include, but are not limited to: reduced density, such as to reduce weight; increased chemical compatibility with gases, such as methane and hydrogen, at high temperatures; thermal stability; thermal conductivity; hardness, such as to increase robustness and/or dimensional stability; manufacturability; and the like.

As described in FIG. 1A above, retort assembly 102 is configured to form a containment boundary for the one or more gases in retort chamber 104. Once positioned, retort chamber 104 and retort lid 106, in combination with sealing gas assembly 110, may be configured to contain the one or more process gases and substantially prevent the process gases from migrating from the retort volume into another volume, or other gases from migrating into the retort volume. Retort lid 106 is configured to contact a wall of retort chamber 104 at a sealing interface 108 to form a contact seal. For example, a surface of each of retort lid 106 and retort chamber 104 at sealing interface 108 may have a relatively low roughness. Sealing interface 108 may be configured to substantially reduce migration of the gases from retort chamber 104 by ensuring that the pressure outside retort chamber 104 is slightly higher than inside retort chamber 104, such that the small positive pressure differential provided by the sealing gas may substantially prevent outflow of the gases from retort chamber 104. In some examples, a width of a gap at sealing interface 108 between retort chamber 104 and retort lid 106 may be reduced, such as by ensuring both contact surfaces of retort chamber 104 and retort lid 106 are smooth, and that a surface area of contact is increased.

Thermal process system 100 includes one or more process gas inlets 112 for discharging an inlet gas mixture into retort chamber 104 and one or more gas outlets 114 for receiving an outlet gas mixture from retort chamber 104. In the example of FIG. 1B, inlet 112 includes an opening at a first end of retort chamber 104 for discharging the inlet gas mixture into retort chamber 104, while outlet 114 includes an opening at a second, opposite end for receiving gases from retort chamber 104. As a result, gases may flow from process gas inlet 112 through the retort volume within retort chamber 104, including substrate 116, and to gas outlet 114.

In the example of FIG. 1B, retort assembly 102 is configured to house one or more substrates 116 within retort chamber 104 in a spatial arrangement defining channels between and around substrates 116. Each substrate 116 may include a plurality of fibers. Fibers may be configured to operate under operating conditions for pyrolysis of hydrocarbons, and may have a relatively high melting or thermal degradation temperature, so as to maintain structural stability throughout the entire range of possible pyrolysis temperatures, or may have a relatively low material density to reduce a weight of fibrous substrates 116. In some examples, the plurality of fibers may be configured and arranged to remove carbon with reduced soot formation. For example, to increase deposition of carbon and reduce formation of soot, substrates 116 may be configured to provide a sufficiently high surface area for a particular volume of gas, such that intermediates of pyrolyzed hydrocarbons favor surface reactions on the fibers of substrates 116. A variety of materials may be used for fibers including, but not limited to, carbon, zirconium dioxide (zirconia), silicon dioxide (silica), and the like.

Thermal process system 100 includes vessel housing 120 positioned around retort chamber 104 and one or more heating elements 128. Vessel housing 120 is configured to maintain a pressure within retort chamber 104 by forming a pressure boundary for one or more gases in retort chamber 104. Materials used for vessel housing 120 may be selected for relatively low weight, such as aluminum. In some examples, vessel housing 120 may be configured in two or more sections to at least partially disassemble to access one or more components within vessel housing 120. In the example of FIG. 1B, vessel housing 120 includes a top end cap, a body, and a bottom end cap. Adjacent sections of vessel housing 120 may be attached using one or more connectors 122 and hermetically sealed against each other using one or more seals 124 positioned at an interface between adjacent sections of vessel housing 120. For example, connectors 122 may include bolts or other fasteners, and seals 124 may include one or more O-rings.

Thermal process system 100 includes a heating assembly 126 configured to heat retort chamber 104. Heating assembly 126 includes one or more heating elements 128 positioned around retort chamber 104. A variety of heating mechanisms may be used for heating elements 128 including, but not limited to: external or internal resistive heating elements, such as ceramic resistive heater rods; induction heating elements, contact heating elements for resistively heating substrates 116, and the like. Electrical connections 130 for heating assembly 126 may be positioned opposite retort lid 106 or through other interfaces that may not interfere with removal of lid 106 from retort chamber 104.

In some examples, thermal process system 100 includes thermal retention materials surrounding retort chamber 104 and/or retort lid 106 configured to retain heat within retort chamber 104. In some examples, thermal process system 100 may include insulation materials configured to reduce thermal conductive losses from retort chamber 104. In the example of FIG. 1B, thermal process system 100 includes insulation 132 surrounding retort chamber 104 and heating elements 128. In some examples, insulation 132 includes solid insulation material, such as a solid microporous ceramic insulation material capable of working temperatures up to about 1200° C.

In addition to thermal management structures, such as heating assembly 126 and insulation material 132, positioned within vessel housing 120, thermal process system 100 may include one or more thermal management structures outside vessel housing 120. In the example of FIG. 1B, thermal process system 100 includes a cooling duct 134 positioned around at least a portion of vessel housing 120. Cooling duct 134 is configured to flow cooling air across an outer surface of vessel housing 120. For example, insulative material 232 may be configured to maintain an outer surface of vessel housing 120 at a first temperature, such as about 100° C., while cooling duct 134 may be configured to maintain an outer surface of cooling duct 134 exposed to an environment at a second, lower temperature, such as about 50° C. A variety of materials may be used for cooling duct 134 including, but not limited to, aluminum.

Thermal process system 100 includes sealing gas inlet 113 configured to receive a sealing gas, such as carbon dioxide, into vessel housing 120. Once received by sealing gas inlet 113, the sealing gas may enter a volume defined by vessel housing 120 at a higher pressure than the pressure within retort assembly 102. The sealing gas may flow from the vessel volume through sealing interface 108 into a retort volume of retort assembly 102. Thermal process system 100 includes sealing gas assembly 110 fluidically coupled to sealing gas inlet 113. Sealing gas assembly 110 includes a control valve 138 and a flow meter 136. Control valve 138 is configured to control a flow of the sealing gas into vessel housing 120. Control valve 138 may be configured to control the flow of the sealing gas into vessel housing 120 to substantially prevent outflow of one or more process gases from retort assembly 102. Flow meter 136 is configured to measure the flow of the sealing gas into vessel housing 120. Thermal process system 100 includes leak gas detector 111 fluidically coupled to gas outlet 114 and configured to detect a leak gas, such as nitrogen gas, in the gases discharged from gas outlet 114.

In some instances, thermal process systems described herein may be utilized in aerospace applications, such as spacecraft. For example, a spacecraft may include a resource-limited and weight- and volume-sensitive environment for which resources like oxygen and water may be preserved in closed loop processes. The thermal process systems described herein may be used for various high temperature processes intended to preserve resources within this environment, such as a pyrolysis reactor for methane pyrolysis.

Figures 2A, 2B:
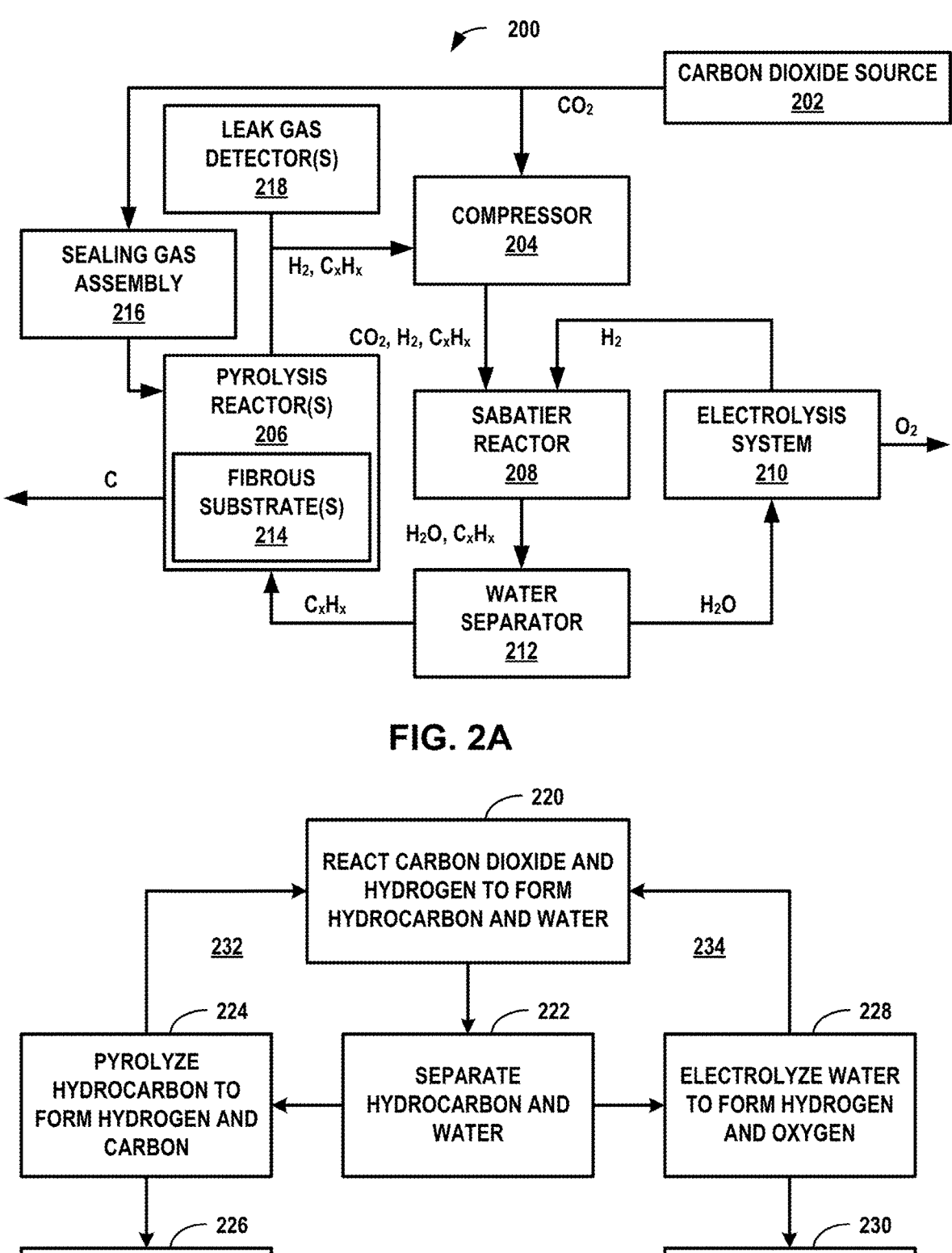
FIG. 2A is a schematic block diagram illustrating an example system for generating oxygen from carbon dioxide.
FIG. 2B is a flowchart of an example technique for generating oxygen from carbon dioxide.

FIG. 2A is a schematic block diagram illustrating an example system 200 for generating oxygen from carbon dioxide produced in a spacecraft. While system 200 will be described with respect to one or more pyrolysis reactors 206, the systems described herein may be used with a variety of thermal processes involving high temperature, pressurized/vacuum process conditions for power, volume, and/or weight sensitive applications.

System 200 may include a carbon dioxide source 202. Carbon dioxide source 202 may be configured to receive carbon dioxide from an environment, such as a spacecraft cabin, concentrate the carbon dioxide for use as a recoverable oxygen source, and discharge purified air back to the spacecraft cabin. For example, carbon dioxide source 202 may include a carbon dioxide removal assembly (CDRA) or other carbon dioxide separation system.

System 200 may include a compressor 204. Compressor 204 may be configured to receive gases from various sources, such as carbon dioxide source 202 and one or more pyrolysis reactors 206, and compress the gases to an operating pressure of a Sabatier reactor 208. For example, Sabatier reactor 208 may operate at relatively higher pressures than carbon dioxide source 202 or pyrolysis reactors 206. In some examples, compressor 204 may be configured to create and maintain a vacuum in pyrolysis reactors 206.

System 200 may include a system for using hydrogen gas, such as Sabatier reactor 208. Sabatier reactor 208 may be configured to receive hydrogen gas, carbon dioxide, and optionally other hydrocarbon gasses, and generate water and hydrocarbons, such as methane and ethane. For example, Sabatier reactor 208 may be configured to receive hydrogen gas from pyrolysis reactors 206 and an electrolysis system 210, and carbon dioxide from carbon dioxide source 202, as well as other hydrocarbon gases, such as unreacted saturated hydrocarbons or byproduct unsaturated hydrocarbons from pyrolysis reactors 206. Sabatier reactor 208 may be configured to operate at a relatively moderate temperature and pressure, such as about 400° C. and about 100 kPa, and may include a catalyst or other rate-enhancing material or structure. Sabatier reactor 208 may be configured to operate according to the following exothermic reaction:

$$CO_2(g)+4H_2(g)\rightarrow CH_4(g)+2H_2O(g)$$

System 200 may include a water separator 212 downstream of Sabatier reactor 208. Water separator 212 may be configured to receive water and hydrocarbons, such as methane and ethane, from Sabatier reactor 208 and separate the water from the hydrocarbons. Water separator 212 may be configured to discharge at least a portion of the water to electrolysis system 210 and at least a portion of the hydrocarbons to pyrolysis reactors 206. In some instances, a water discharged to pyrolysis reactors 206 may be substantially low (e.g., less than 1 vol. %). A variety of water separators may be used including, but not limited to, condensers, centrifugal separators, membranes (e.g., zeolite membranes), and the like.

As one hydrogen source for Sabatier reactor 208, system 200 may include an oxygen generation assembly, such as electrolysis system 210. Electrolysis system 210 may be configured to receive water from various sources, such as Sabatier reactor 208 or a potable water source and generate oxygen gas and hydrogen gas from the water. Electrolysis system 210 may be configured to discharge the hydrogen gas back to Sabatier reactor 208 and discharge oxygen gas to a storage or pressurization system for use in one or more environments. Electrolysis system 210 may be configured to operate according to the following reaction:

$$2H_2O(g/l)\rightarrow 2H_2(g)+O_2(g)$$

As described above, water separator 212 may be configured to discharge hydrocarbons generated from Sabatier reactor 208 to one or more pyrolysis reactors 206. System 200 may be configured to preserve at least a portion of the hydrogen present in hydrocarbons from Sabatier reactor 208 by sending the hydrocarbons through one or more pyrolysis reactors 206 to produce hydrogen gas.

Pyrolysis reactor(s) 206 may each be configured to generate hydrogen gas from hydrocarbons through pyrolysis. In the example of FIG. 2A, pyrolysis reactors 206 may be configured to generate hydrogen gas and carbon from methane, such as according to the following endothermic reaction:

$$CH_4(g) \rightarrow 2H_2(g)+C(s)$$

In some examples, each pyrolysis reactor 206 may include one or more fibrous substrates 214. Each fibrous substrate 214 may be configured to provide a deposition surface for carbon generated from the pyrolysis of the hydrocarbons. In some examples, fibrous substrates 214 may be configured to be removable from pyrolysis reactors 206 once spent and replaced with a new fibrous substrate 214.

As described above with respect to thermal process system 100 of FIGS. 1A and 1B, pyrolysis reactor 206 may be configured with separate pressure and gas containment boundaries, such that pyrolysis reactors 206 may operate with lower power and/or have lower weight and/or volume. For example, an outer vessel housing may maintain a pressurized or vacuum environment, and an inner retort assembly positioned, heated, and insulated within the outer vessel housing may contain the gases at high temperature. As a result, pyrolysis reactor 206 may be operated at temperature and pressure conditions that enable high recovery of carbon with reduced power input.

System 200 may include a sealing gas assembly 216 fluidically coupled to pyrolysis reactor 206 and carbon dioxide source 202. Sealing gas assembly 216 may be configured to control flow of carbon dioxide from carbon dioxide source 202 into pyrolysis reactor 206. Under a positive pressure differential, carbon dioxide may flow across a non-hermetic seal to substantially reduce or prevent hydrocarbons and hydrogen gas from flowing out of pyrolysis reactor 206. The carbon dioxide may not substantially react with the hydrocarbon reactants or hydrogen gas product under the operating conditions in pyrolysis reactor 206. The carbon dioxide may be discharged with the hydrogen gas and any remaining hydrocarbons to compressor 204 and used as a precursor reactant with hydrogen gas and additional carbon dioxide in Sabatier reactor 208 under different operating conditions to produce methane and water.

System 200 may include leak gas detector 218 fluidically coupled to piping or components in system 200. In the example of FIG. 2A, leak gas detector 218 is positioned downstream of pyrolysis reactor 206, as pyrolysis reactor 206 is typically under vacuum and more susceptible to inflow leaks than other components in system 200. However, leak gas detector 218, or additional leak gas detectors, may be positioned at other locations in system 200. Leak gas detector 218 is configured to detect a presence or concentration of nitrogen gas in one or more gas streams in system 200. For example, a leak formed in an outer pressure boundary of pyrolysis reactor 206 may result in nitrogen gas present in an ambient atmosphere flowing into pyrolysis reactor 206 when pyrolysis reactor 206 is at vacuum conditions. Leak gas detector 218 may detect the nitrogen gas and output an indication, such as an alarm or digital output representing the presence or concentration of the nitrogen gas. In some examples, leak gas detector 218 may be communicatively coupled to one or more interlocks that modify operation of pyrolysis reactor 206 based on the presence or concentration of nitrogen gas, such as shutdown operations as a result of a severe leak indicated by leak gas detector 218.

FIG. 2B is a flowchart of an example technique for generating oxygen from carbon dioxide. The example technique of FIG. 2B will be described with reference to system 200 of FIG. 2A; however, the example technique of FIG. 2B may be performed by other systems. The technique of FIG. 2B includes a carbon recovery cycle 232 and an oxygen recovery cycle 234. While carbon recovery cycle 232 and oxygen recovery cycle 234 will be referred to as separate cycles based on discharged products, it will be understood that hydrogen may be recovered in both cycles 232 and 234, and that recovery of hydrogen in both cycles may enable more complete recovery of oxygen and/or carbon in cycles 234 and 232, respectively.

In both carbon recovery cycle 232 and oxygen recovery cycle 234, Sabatier reactor 208 may react carbon dioxide and hydrogen to form one or more hydrocarbons and water (220). For example, Sabatier reactor 208 may receive carbon dioxide from carbon dioxide source 202 and hydrogen gas and, optionally, hydrocarbons from pyrolysis reactors 206 via compressor 204. Sabatier reactor 208 may react the carbon dioxide and hydrogen gas under operating conditions, such as about 400° C. and about 100 kPa. Sabatier reactor 208 may discharge water and hydrocarbons, such as methane and ethane, to water separator 212.

Water separator 212 may separate hydrocarbons and water (222). For example, water separator 212 may receive hydrocarbons and water from Sabatier reactor 208 and use one or more phase change, filtration, or other separation processes to separate hydrocarbons and water. Water separator 212 may discharge at least a portion of the hydrocarbons to pyrolysis reactors 206 and at least a portion of the water to electrolysis system 228. In some examples, the stream discharged to pyrolysis reactors 206 includes less than 1 vol. % water.

In oxygen recovery cycle 234, electrolysis system 228 may electrolyze water to hydrogen and oxygen (228). For example, electrolysis system 228 may receive water from Sabatier reactor 208 via water separator 212, and optionally other water sources such as dehumidification systems. Electrolysis system 228 may discharge hydrogen gas back to Sabatier reactor 208 to further react with carbon dioxide (220). In some examples, the hydrogen gas generated from electrolysis system 228 may account for about half (e.g., between about 40% and about 60%) of the hydrogen gas reacted in Sabatier reactor 208. Electrolysis system 228 may discharge oxygen to a cabin (230) or storage system to complete recovery of the oxygen received as carbon dioxide.

In carbon recovery cycle 232, pyrolysis reactors 206 may pyrolyze hydrocarbons to form hydrogen and carbon (224). For example, pyrolysis reactors 206 may receive hydrocarbons from Sabatier reactor 208 via water separator 212 and pyrolyze the hydrocarbons under pyrolysis operating conditions, such as a temperature between about 850° C. and about 1300° C., and preferably between about 1050° C. and about 1200° C., and a pressure between about 1 kPa and about 65 kPa, and preferably between about 7 kPa and about 30 kPa, to form hydrogen gas and carbon. As discussed above, sealing gas assembly 216 may maintain a flow of carbon dioxide into pyrolysis reactor 206 to substantially prevent outflow of the hydrocarbons and hydrogen gas at the thermal process conditions. Pyrolysis reactors 206 may discharge hydrogen gas, and optionally unreacted or partially reacted hydrocarbons, to Sabatier reactor 208 to further react with carbon dioxide (220). Pyrolysis reactors 206 may capture the carbon in fibrous substrates 214 (226), which may be removed from pyrolysis reactors 206 at an end of an operating life (e.g., initiation of soot formation), replaced, and stored.

FIG. 3A is a flowchart of an example technique for thermally processing gases. Reference will be made to thermal process system 100 of FIG. 1B; however, other thermal process systems may be used to perform the technique of FIG. 3A. The method includes receiving process gases into retort chamber 104 (300). Process gases may include any gases that undergo or result from a thermal process. The method includes receiving a sealing into vessel housing 120 (302). The sealing gas may be at a higher pressure than a pressure within retort chamber 104 to maintain a positive pressure differential across sealing interface 108.

The method includes maintaining a retort volume within retort chamber 104 at thermal process conditions (304). Controller 109 of FIG. 1A may operate heating elements 128 to maintain a temperature of the retort volume within retort chamber 104 above a threshold temperature, such as about 400° C. (e.g., within control or equipment error, such as +/−25° C.) (306), which may be substantially higher than conventional seals, but within an operating range of a contact seal formed by retort chamber 104 and retort lid 106. Controller 109 may control a pressure or vacuum of process gas streams received by process gas inlet 112 and/or discharged by gas outlet 114. Vessel housing 120 may maintain the pressure boundary of retort assembly 102 (308).

Retort chamber 104 and retort lid 106 may seal against each other at sealing interface 108 to contain gases within the retort volume. To further prevent process gases from escaping through sealing interface 108, the method includes maintaining a flow of sealing gas into retort assembly 102 (310). Controller 109 may operate sealing gas assembly 110, such as control valve 138, to maintain flow of the sealing gas into the retort volume of retort chamber 104. As one example, controller 109 may maintain a particular flow rate of the sealing gas into retort chamber 104, including during transient conditions when one or more process variations may cause a temporary increase in pressure within retort chamber 104. As another example, controller 109 may maintain a particular pressure of the sealing gas that is greater than a pressure within the retort volume, or maintain a particular pressure differential across sealing interface 108. The pressure or pressure differential may be sufficiently high to substantially prevent outflow of the one or more process gases from retort assembly 102. For example, for anticipated pressure spikes of up to 100 torr, controller 109 may maintain the pressure of the sealing gas to create a pressure differential greater than about 100 torr (e.g., within control or equipment error, such as +/−10 torr) above a pressure within retort chamber 104. In some thermal processes involving a vacuum within retort assembly 102, no compression may be required for the sealing gas, as the vacuum within retort assembly 102 may provide sufficient pressure differential to drive flow of the sealing gas across sealing interface 108.

The method may include monitoring a process stream, such as gases discharged from gas outlet 114, for a leak gas (312). For example, rather than only monitor for leaks at start-up, controller 109 may receive a measurement signal from leak gas detector 111 that indicates a concentration of a leak gas in the process stream. If the concentration exceeds a threshold related to a concentration or increase in concentration of the leak gas in the process stream, leak gas detector 111 may output an indication of the leak gas. Depending on a location of the process stream monitored by leak gas detector 111, the indication may include an anticipated location of the leak. As one example, controller 109 may receive measurement signals from a single leak gas detector 111 that indicates whether a leak is present in thermal process system 100 or other systems fluidically coupled upstream of thermal process system 100. As another example, controller 109 may receive measurement signals from leak gas detectors positioned at two or more different locations within a system, such as at process gas inlet 112 and gas outlet 114, that indicates an anticipated location of the leak based on a higher concentration of the leak gas at a particular location.

FIG. 3B is a flowchart of an example technique for pyrolyzing hydrocarbons. Reference will be made to thermal process system 100 of FIG. 1B; however, other thermal process systems may be used to perform the technique of FIG. 3B. The method includes receiving hydrocarbons into retort chamber 104 (320) and receiving carbon dioxide into vessel housing 120 (322). The method includes maintaining a retort volume within retort chamber 104 at pyrolysis conditions (324), such that methane is consumed to form hydrogen gas and carbon. For example, controller 109 may operate heating elements 128 to maintain a temperature of the retort volume within retort chamber 104 above a threshold temperature, such as about 850° C. (e.g., within control or equipment error, such as +/−25° C.) (326). Controller 109 may control a vacuum of methane and/or hydrogen gas streams received by inlet 112 and/or discharged by outlet 114 (328). Vessel housing 120 may maintain the pressure or vacuum within the reactor volume. Controller 109 may operate sealing gas assembly 110 to maintain flow of carbon dioxide into the retort volume (330). Retort chamber 104 and retort lid 106 may seal against each other to contain methane and hydrogen gas within the retort volume. Controller 109 may monitor one or more process streams for nitrogen gas, such as through measurement signals received from leak gas detector 111 (332). Once the carbon has substantially loaded substrate 116, substrates 116 may be removed from retort chamber 104 (334).

The following numbered clauses may demonstrate one or more aspects of the disclosure.

Clause 1: A thermal process system includes a retort assembly comprising a retort chamber and configured to substantially contain one or more process gases in the retort chamber during a thermal process; a heating assembly comprising one or more heating elements and configured to heat the retort chamber; a vessel housing positioned around the retort chamber and the one or more heating elements and configured to maintain a pressure within the retort chamber; a process gas inlet configured to receive the one or more process gases into the retort assembly; and a sealing gas inlet configured to receive a sealing gas into the vessel housing.

Clause 2: The thermal process system of clause 1, wherein the sealing gas comprises at least one of the one or more process gases, a precursor to the one or more process gases, or a derivative of the one or more process gases in the retort chamber.

Clause 3: The thermal process system of either of clauses 1 or 2, further includes a gas outlet configured to discharge one or more process gases from the retort chamber; and a leak gas detector downstream of the gas outlet and configured to detect a presence of a leak gas, wherein the leak gas comprises a gas that is not the one or more process gases in the retort chamber.

Clause 4: The thermal process system of clause 3, wherein the sealing gas comprises carbon dioxide, and wherein the leak gas comprises nitrogen.

Clause 5: The thermal process system of any of clauses 1 through 4, further includes a control valve configured to control a flow of the sealing gas into the vessel housing; and a flow meter configured to measure the flow of the sealing gas into the vessel housing.

Clause 6: The thermal process system of clause 5, wherein the control valve is configured to control the flow of the sealing gas into the vessel housing to substantially prevent outflow of the one or more process gases from the retort assembly.

Clause 7: The thermal process system of any of clauses 1 through 6, wherein the retort assembly is configured to form a concentration or partial pressure boundary for the one or more process gases in the retort chamber, and wherein the vessel housing is configured to form a pressure boundary between an interior volume of the vessel housing and an external environment.

Clause 8: The thermal process system of any of clauses 1 through 7, wherein the retort assembly further comprises a removable retort lid configured to contact a wall of the retort chamber at a sealing interface, and wherein the sealing interface between the retort lid and the retort chamber is configured to form a contact seal.

Clause 9: The thermal process system of clause 8, wherein the contact seal is non-hermetic and does not include a gasket.

Clause 10: The thermal process system of any of clauses 1 through 9, further comprising insulation material surrounding the retort chamber.

Clause 11: A system for recovering carbon includes a pyrolysis reactor configured to generate hydrogen gas from a hydrocarbon through pyrolysis, wherein the pyrolysis reactor comprises: a retort assembly includes substantially contain the hydrocarbon and the hydrogen gas in the retort chamber during the pyrolysis; and house one or more fibrous substrates defining a deposition surface for the carbon generated from the pyrolysis; a heating assembly comprising one or more heating elements and configured to heat the retort chamber; and a vessel housing positioned around the retort chamber and the one or more heating elements and configured to maintain a pressure within the retort chamber; a process gas inlet configured to receive the hydrocarbon into the retort chamber; and a carbon dioxide inlet configured to receive carbon dioxide from a carbon dioxide source into the vessel housing.

Clause 12: The system of clause 11, wherein the hydrocarbon is methane, wherein the pyrolysis reactor is configured to generate carbon and hydrogen gas from the methane, and wherein the system further comprises a Sabatier reactor configured to: receive a portion of hydrogen gas and a first portion of carbon dioxide from the pyrolysis reactor; receive a second portion of carbon dioxide from the carbon dioxide source; generate the methane and water from the first and second portions of carbon dioxide and the portion of hydrogen gas; and discharge the methane to the pyrolysis reactor.

Clause 13: The system of clause 12, wherein the portion of hydrogen gas is a first portion of hydrogen gas, and wherein the system further comprises an oxygen generation system configured to: receive the water from the Sabatier reactor; generate oxygen and a second portion of hydrogen gas from the water; and discharge the second portion of hydrogen gas to the Sabatier reactor.

Clause 14: The system of any of clauses 11 through 13, wherein the pyrolysis reactor comprises a gas outlet configured to discharge one or more process gases from the retort chamber, and wherein the system comprises a leak gas detector downstream of the gas outlet, wherein the leak gas detector is configured to detect a presence of a leak gas, and wherein the leak gas comprises a gas that is not a hydrocarbon.

Clause 15: The system of clause 14, wherein the leak gas comprises nitrogen gas.

Clause 16: The system of any of clauses 11 through 15, wherein the pyrolysis reactor is configured to maintain a temperature of the retort chamber greater than about 850° C. during pyrolysis, and wherein the vessel housing is configured to maintain a pressure of the retort chamber less than about 100 torr during pyrolysis.

Clause 17: A method includes receiving, by a retort chamber of a retort assembly of a thermal process system, one or more process gases; receiving, by a vessel housing positioned around the retort chamber, a sealing gas; maintaining, by the thermal process system, the one or more process gases at thermal process conditions in the retort chamber by at least: maintaining a temperature of the one or more process gases in a retort volume within the retort chamber above about 400° C.; maintaining a pressure boundary between a vessel volume within the vessel housing and an environment external to the vessel housing; and maintaining a flow of the sealing gas from the vessel volume into the retort volume to substantially prevent outflow of the one or more process gases at the thermal process conditions.

Clause 18: The method of clause 17, wherein the sealing gas comprises at least one of the one or more process gases, a precursor to the one or more process gases, or a derivative of the one or more process gases in the retort chamber.

Clause 19: The method of either of clauses 17 or 18, further comprising detecting, by a leak gas detector downstream of the thermal process system, a presence of a leak gas, wherein the leak gas comprises a gas that is not the one or more process gases in the retort chamber.

Clause 20: The method of clause 19, wherein the sealing gas comprises carbon dioxide, and wherein the leak gas comprises nitrogen.

In one or more examples, the thermal process system described herein may utilize hardware, software, firmware, or any combination thereof for achieving the functions described, such as controller 109 and/or lead gas detector 111. Those functions implemented in software may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure.

Instructions may be executed by one or more processors within the control circuitry or communicatively coupled to the control circuitry. The one or more processors may, for example, include one or more DSPs, general purpose microprocessors, application specific integrated circuits ASICs, FPGAs, or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for performing the techniques described herein. Also, the techniques could be fully implemented in one or more circuits or logic elements.

The techniques of this disclosure may be implemented in a wide variety of devices or apparatuses that include integrated circuits (ICs) or sets of ICs (e.g., chip sets). Various components, modules, or units are described in this disclosure to emphasize functional aspects of devices configured to perform the disclosed techniques, but do not necessarily require realization by different hardware units. Rather, various units may be combined or provided by a collection of interoperative hardware units, including one or more processors as described above, in conjunction with suitable software and/or firmware.

Various examples have been described. These and other examples are within the scope of the following claims.

What is claimed is:

1. A thermal process system, comprising:
a retort assembly configured to substantially contain one or more process gases in a retort chamber during a thermal process;
a heating assembly comprising one or more heating elements and configured to heat the retort chamber;
a vessel housing positioned around the retort chamber and the one or more heating elements and configured to maintain a pressure or vacuum within the retort chamber;
a process gas inlet configured to receive the one or more process gases into the retort assembly; and
a sealing gas inlet configured to receive a sealing gas into the vessel housing,
wherein the retort assembly comprises:
the retort chamber; and
a removable retort lid configured to contact a wall of the retort chamber at a sealing interface, and
wherein the sealing interface between the removable retort lid and the retort chamber is configured to form a non-hermetic contact seal.

2. The thermal process system of claim 1, wherein the sealing gas comprises at least one of the one or more process gases, a precursor to the one or more process gases, or a derivative of the one or more process gases in the retort chamber.

3. The thermal process system of claim 1, further comprising:
a gas outlet configured to discharge one or more process gases from the retort chamber out of the thermal process system; and
a leak gas detector downstream of the gas outlet and configured to detect a presence of a leak gas, wherein the leak gas comprises a gas that is not the one or more process gases in the retort chamber.

4. The thermal process system of claim 3,
wherein the sealing gas comprises carbon dioxide, and
wherein the leak gas comprises nitrogen.

5. The thermal process system of claim 1, further comprising a sealing gas assembly comprising:
a control valve configured to control a flow of the sealing gas into the vessel housing; and
a flow meter configured to measure the flow of the sealing gas into the vessel housing.

6. The thermal process system of claim 5, wherein the control valve is configured to control the flow of the sealing gas into the vessel housing to substantially prevent outflow of the one or more process gases from the retort assembly.

7. The thermal process system of claim 1,
wherein the retort assembly is configured to form a concentration or partial pressure boundary for the one or more process gases in the retort chamber, and
wherein the vessel housing is configured to form a pressure boundary between an interior volume of the vessel housing and an external environment.

8. The thermal process system of claim 1, further comprising insulation material surrounding the retort chamber.

9. The thermal process system of claim 1, wherein the non-hermetic contact seal does not include a gasket.

10. A thermal process system, comprising:
a retort assembly comprising a retort chamber and configured to substantially contain one or more process gases in the retort chamber during a thermal process;
a heating assembly comprising one or more heating elements and configured to heat the retort chamber;
a vessel housing positioned around the retort chamber and the one or more heating elements and configured to maintain a pressure or vacuum within the retort chamber;
a process gas inlet configured to receive the one or more process gases into the retort assembly;
a sealing gas inlet configured to receive a sealing gas into the vessel housing;
a gas outlet configured to discharge one or more process gases from the retort assembly out of the thermal process system; and
a leak gas detector downstream of the gas outlet and configured to detect a presence of a leak gas.

11. A system for recovering carbon, comprising:
a pyrolysis reactor configured to generate hydrogen gas from a hydrocarbon through pyrolysis, wherein the pyrolysis reactor comprises:
a retort assembly configured to:
substantially contain the hydrocarbon and the hydrogen gas in a retort chamber during the pyrolysis; and
house one or more fibrous substrates defining a deposition surface for carbon generated from the pyrolysis of the hydrocarbon;
a heating assembly comprising one or more heating elements and configured to heat the retort chamber; and
a vessel housing positioned around the retort chamber and the one or more heating elements and configured to maintain a pressure or vacuum within the retort chamber;
a process gas inlet configured to receive the hydrocarbon into the retort chamber; and
a carbon dioxide inlet configured to receive carbon dioxide from a carbon dioxide source into the vessel housing,
wherein the retort assembly comprises:
the retort chamber; and
a removable retort lid configured to contact a wall of the retort chamber at a sealing interface, and
wherein the sealing interface between the removable retort lid and the retort chamber is configured to form a non-hermetic contact seal.

12. The system of claim 11,
wherein the hydrocarbon is methane,
wherein the pyrolysis reactor is configured to generate carbon and hydrogen gas from the methane, and
wherein the system further comprises a Sabatier reactor configured to:
receive a portion of hydrogen gas and a first portion of carbon dioxide from the pyrolysis reactor;

receive a second portion of carbon dioxide from the carbon dioxide source;

generate the methane and water from the first and second portions of carbon dioxide and the portion of hydrogen gas; and discharge the methane to the pyrolysis reactor.

13. The system of claim 12, wherein the portion of hydrogen gas is a first portion of hydrogen gas, and wherein the system further comprises an oxygen generation system configured to:

receive the water from the Sabatier reactor;

generate oxygen and a second portion of hydrogen gas from the water; and discharge the second portion of hydrogen gas to the Sabatier reactor.

14. The system of claim 11, wherein the pyrolysis reactor comprises a gas outlet configured to discharge one or more process gases from the retort chamber out of the system, and wherein the system comprises a leak gas detector downstream of the gas outlet, wherein the leak gas detector is configured to detect a presence of a leak gas, and wherein the leak gas comprises a gas that is not a hydrocarbon.

15. The system of claim 14, wherein the leak gas comprises nitrogen gas.

16. The system of claim 11, wherein the pyrolysis reactor is configured to maintain a temperature of the retort chamber greater than about 850° C. during pyrolysis, and wherein the vessel housing is configured to maintain a pressure or vacuum of the retort chamber less than about 100 torr during pyrolysis.

17. A method, comprising:

receiving, by a retort chamber of a retort assembly of a thermal process system, one or more process gases, wherein the retort assembly comprises the retort chamber and a removable retort lid configured to contact a wall of the retort chamber at a sealing interface, and wherein the sealing interface between the removable retort lid and the retort chamber is configured to form a non-hermetic contact seal;

receiving, by a vessel housing positioned around the retort chamber, a sealing gas;

maintaining, by the thermal process system, the one or more process gases at thermal process conditions in the retort chamber by at least:

maintaining a temperature of the one or more process gases in a retort volume within the retort chamber above about 400° C.;

maintaining a pressure boundary between a vessel volume within the vessel housing and an environment external to the vessel housing; and maintaining a flow of the sealing gas from the vessel volume into the retort volume to substantially prevent outflow of the one or more process gases at the thermal process conditions.

18. The method of claim 17, wherein the sealing gas comprises at least one of the one or more process gases, a precursor to the one or more process gases, or a derivative of the one or more process gases in the retort chamber.

19. The method of claim 17, further comprising detecting, by a leak gas detector downstream of the thermal process system, a presence of a leak gas, wherein the leak gas comprises a gas that is not the one or more process gases in the retort chamber.

20. The method of claim 19, wherein the sealing gas comprises carbon dioxide, and wherein the leak gas comprises nitrogen.

* * * * *